United States Patent
Warscheild et al.

(10) Patent No.: US 8,071,329 B2
(45) Date of Patent: Dec. 6, 2011

(54) ANALYZING AND DISTINGUISHING ORGANISMS SUCH AS BACTERIAL SPORES BY THEIR SOLUBLE POLYPEPTIDES

(75) Inventors: Bettina Warscheild, Dortmund (DE); Catherine Fenselau, Baltimore, MD (US)

(73) Assignee: University of Maryland, College Park, MD (US)

( * ) Notice: Subject to any disclaimer, the term of this patent is extended or adjusted under 35 U.S.C. 154(b) by 238 days.

(21) Appl. No.: 10/683,128

(22) Filed: Oct. 14, 2003

(65) Prior Publication Data

US 2005/0032040 A1 Feb. 10, 2005

Related U.S. Application Data

(60) Provisional application No. 60/417,792, filed on Oct. 11, 2002.

(51) Int. Cl.
*C12Q 1/04* (2006.01)
(52) U.S. Cl. ......... 435/34

(58) Field of Classification Search .......... None
See application file for complete search history.

(56) References Cited

U.S. PATENT DOCUMENTS

2002/0123055 A1* 9/2002 Estell et al. .......... 435/6

OTHER PUBLICATIONS

Krishnamurty et al., Rapid Commun. Mass Spectrom., 10:883-888, 1996.*
Krishnamurthy et al., J. Toxicol. Toxin Rev., 19:95-117, 2000.*
Demirev et al., Anal. Chem., 71:2732-2738, 1999.*
Russell et al. (Anal. Chem. 73:2682-2685, 2001).*
Wang et al. (Rapid Comm. Mass Spec., 14:1377-1383, 2000).*

* cited by examiner

*Primary Examiner* — Nita M Minnifield
*Assistant Examiner* — Brian J Gangle
(74) *Attorney, Agent, or Firm* — Arent Fox, LLP (57) ABSTRACT

Organisms such as bacterial spores are analyzed and/or characterized based on based on peptide fragments of a set of selectively solublizede proteins. Libraries of protein and gene sequences may be utilized for comparison to and identification of proteins and unknown organisms.

15 Claims, 8 Drawing Sheets

Figure 1: Strategy for rapid identification of *Bacillus* spores and their mixtures by spore lysis on the sample holder, in situ proteolysis, $MS^n$ analysis and database searching.

Figure 2: MALDI-TOFMS spectra from polypeptide ions (2 a) and tryptic peptide ions (2 b) generated *in situ* from *B. anthracis Sterne* spores.

Figure 3: MALDI-TOFMS spectrum of peptide ions generated *in situ* from a 3:1 spore mixture of *B. thuringiensis* and *B. globigii*.

Figure 4: PSD spectra from peptide ions at m/z 1929 (3a) and m/z 1940 (3b) derived from a 3:1 spore mixture of *B. thuringiensis* and *B. globigii*.

Figure 5: MALDI-TOFMS spectrum of tryptic peptides generated *in situ* from a 1:1 spore mixture of *B. anthracis sterne* and *B. thuriengiensis*.

Figure 6: Post source decay mass spectrum of the tryptic peptide at m/z 1519.

ANALYZING AND DISTINGUISHING ORGANISMS SUCH AS BACTERIAL SPORES BY THEIR SOLUBLE POLYPEPTIDES

CROSS-REFERENCE TO RELATED APPLICATIONS

This application claims the benefit of U.S. Provisional Application No. 60/417,792, filed Oct. 11, 2002.

STATEMENT REGARDING FEDERALLY SPONSORED RESEARCH AND DEVELOPMENT

The U.S. Government has a paid-up license in this invention and the right in limited circumstances to require the patent owner to license others on reasonable terms as provided by the terms of a contract awarded by The Defense Advanced Research Agency.

BACKGROUND OF THE INVENTION (1) Field of the Invention

The invention relates to analyzing organisms such as bacterial spores based on their soluble polypeptides and more particularly to the identification of organisms such as bacterial spores based on peptide fragments of their soluble polypeptides.

(2) Description of Related Art

A number of approaches have been used in the past for applying the analytic power of mass spectrometry to microorganisms (Fenselau and Demirev, Mass Spectrom Rev 20, 157). Among these, electrospray ionization and matrix assisted laser desorption mass spectrometry have provided access to cellular proteins as biomarkers. In many cases proteins have first been isolated from other bacterial material for subsequent analysis by enzymatic, chromatographic and mass spectral procedures (Harris and Reilly, Anal Chem 74, 4410, 2002; Cargile, McLuckey and Stephenson, Anal Chem 73, 1277, 2001; Zhou et al, Proteomics 1, 683, 2001; Krishnamurthy et al, J. Toxicol. Toxin Rev 19, 95, 2000; Xiang et al, Anal Chem 72, 2475, 2000; Arnold and Reilly, Anal Biochem 269, 105, 1999; Holland et al Anal Chem 71, 3226, 1999; Yates and Eng, U.S. Pat. No. 5,538,897; Dai et al, Rapid Commun Mass Spectrom 13, 73, 1999; Liu et al, Anal Chem 70, 1797, 1998; Despeyroux, Phillpotts and Watts, Rapid Commun Mass Spectrom 10, 937, 1996; Cain et al, Rapid Commun. Mass Spectrom 8, 1026, 1994). Isolated proteins were cleaved to peptides, the peptides were partially sequenced by tandem mass spectrometry, and the parent proteins were identified by standard protein and genome database searches. The bacteria species were characterized from the database as the source of the proteins. In other cases researchers have undertaken to analyze protein biomarkers without a separation step (Claydon et al Nature Biotechnol. 14, 1584, 1996; Demirev and Fenselau PCT/US 99/27191; Holland et al, Rapid Commun. Mass Spectrom 10, 1227, 1996; Krishnamurthy, Ross and Rajamani, Rapid Commun. Mass Spetrom 10, 883, 1996; Krishnamurthy U.S. Pat. No. 6,177,266). The sample is lysed on the mass spectrometry sample holder (in situ) and proteins are desorbed directly by matrix assisted laser desorption ionization (MALDI). The spectrum of the mixture of proteins detected can be matched to a carefully prepared library of microbial mass spectra (Conway et al, J. Mol. Microbiol Biotechnol. 3, 103, 2001; Jarman et al, Anal Chem 72, 1217, 2000), allowing distinction of the species, or the microorganism can be characterized by matching the masses of the suite of proteins observed to protein masses predicted from the genome (Demirev et al, Anal Chem 73, 4566, 2001; Pineda et al, Anal Chem 72, 3739, 2000; Demirev et al, Anal Chem 71, 2732, 1999; Demirev and Fenselau PTC/US99/27191).

More recently enzymatic cleavage of proteins on the sample holder for direct analysis of peptides (Yao, Demirev and Fenselau, Anal Chem 74, 2529, 2002; Yao and Fenselau, Rapid Commun Mass Spectrom 16, 1953, 2002) has been proposed to provide a simple rapid analysis of simple viruses. Applying this strategy to more complex microorganisms (*Escherichia coli* and *Erwinia herbicola*) has revealed that indiscriminant enzymatic digestion of proteins in a microorganism, without a fractionation step, produces a large mixture of peptides, poor signal to noise ratios, poor sensitivity for tandem mass spectrometry (sequencing) experiments, and poor reproducibility. Also see "Rapid Microorganism Identification by MALDI Mass Spectrometry and Model-derived Ribosomal Protein Biomarkers" Antoine et al., J. Lin, Anal. Chem. 75 (2003) pp 3817-3822; U.S. Pat. No. 6,558,946 to Krishnamurthy and U.S. Pat. No. 6,177,266 to Krishnamurthy et al.; and U.S. Patent Application 20030027231 to Bryden et al.

Among the microorganisms, spores of the genus *Bacillus* are monitored as important targets in battle spaces, subways and buildings, counter-terrorism activities, and in some medical diagnosis. Direct desorption of biomarker proteins from spores has been challenging, as the outer spore coat is strongly resistant to solvents. Abundant proteins, however, are present within the spore core. These proteins can be extracted from spores by treatment with 1N H; 1 HCl, and hence they are referred in the art to as small, acid-soluble proteins (SASP). Their sequences are different for different spores (Hathout et al, Applied Environ. Microbiology 69, in press, 2003).

Also see WO 02/40678 A1 to Fairhead for a detailed description of small acid-soluble spore proteins, which is hereby incorporated by reference in its entirety.

BRIEF SUMMARY OF THE INVENTION

This invention combines selective solubilization of proteins such as SASPs on a sample holder, with rapid enzymatic digestion in situ, partial sequencing by mass spectrometry and database searching to characterize organisms such as *Bacillus* spores, that may be contained in mixtures, and to distinguish closely related species and strains.

Some embodiments of this invention are directed to a method of analyzing single cell organisms or microorganisms, comprising the steps of:

preparing a sample of at least one single cell organism or microorganism;

adding a solvent to said sample to extract small, acid-soluble proteins from the sample;

digesting the small, acid-soluble proteins, with a proteolytic enzyme or with a chemical reagent that cleaves proteins at specific residues, to produce peptide fragments; and subjecting the peptide fragments to mass spectrometry or tandem mass spectrometric analysis.

In some embodiments of this invention, the single cell organism or microorganism is at least one member selected from the group consisting of bacterial spores, Gram positive vegetative bacteria, Gram negative vegetative bacteria, virus, fungus, single cell parasites, pollen and any mixtures thereof.

In some embodiments of this invention, the solvent is at least one member selected from the group consisting of an acid, acetic acid, trifluoroacetic acid, formic acid, nitric acid, hydrochloric acid, hydrofluoric acid, methanol, ammonium acetate and any mixtures thereof.

In some embodiments of this invention, the proteolytic enzyme is selected from the group consisting of trypsin, chymotrypsin, pepsin, subtilisin, papain, elastase, *S. aureus* V8, Lys-C endoproteinase, Arg-C endoproteinase, and Glu-C endoproteinase; or the chemical cleaving agent is selected from the group consisting of BNPS-skatole and cyanogen bromide. The proteolytic enzyme can be immobilized, for example covalently bonded to tiny beads or some other surface so that the enzyme does not "cut" itself up. Also, any protease could be used in this invention.

In some embodiments of this invention, the mass spectrometry can be conducted, for examples, with a matrix-assisted laser desorption ionization, atmospheric matrix assisted laser desorption, medium pressure matrix assisted laser desorption, or with electrospray/nanospray ionization. Lasers of any wavelength in the infrared and ultraviolent ranges may be used.

In some embodiments of this invention, after a step of subjecting the peptide fragments to mass spectrometry, the sequences are determined for at least some of the peptide fragments.

In some embodiments, this invention is directed to a method of distinguishing bacterial spores, comprising the steps of:
 preparing a bacterial spore sample on a mass spectrometry sample holder;
 adding an acid to said sample to extract small, acid-soluble proteins from the sample;
 digesting the small, acid-soluble proteins with proteolytic enzyme to produce peptide fragments;
 subjecting the peptide fragments to mass spectrometry;
 comparing results of the mass spectrometry of the peptide fragments with results of mass spectrometry for known bacterial spore samples, proteins or peptides; and
 identifying the bacterial spore sample by matching the results of the mass spectrometry of the peptide fragments with results of mass spectrometry for peptide fragments from digested small, acid-soluble proteins from at least one bacterial spore sample having a known identity, or with results generated in silico, based on the protein or genome sequence, the known specificity of the enzyme, and/or widely known guidelines for fragmentation of peptides in mass spectrometry and tandem mass spectrometry.

In some embodiments of this invention, the bacterial spore sample contains spores from at least one member of the *Bacillus* genus.

In some embodiments of this invention, in a step of identifying, the results of the mass spectrometry of the peptide fragments of the sample spores are compared with the results of mass spectrometry of peptide fragments of spores of small, acid-soluble proteins previously observed or predicted in silico from at least one *Bacillus* spore species and strain selected from the group consisting of *B. anthracis* Sterne, *B. cereus* T strain, *B. thuringienesis* Kurstaki, *B. mycoides, B. subtilis* strain 168 (ATCC #23857) and *B. globigii*.

In some embodiments of this invention, in a step of identifying, the sample is determined to contain one *Bacillus* spore species and strain selected from the group consisting of *B. anthracis* Sterne, *B. cereus* T strain, *B. thuringienesis* Kurstaki, *B. mycoides, B. subtilis* strain 168 (ATCC #23857) and *B. globigii*.

In some embodiments of this invention, in a step of identifying, the sample is determined to contain at least one *Bacillus* spore species and strains selected from the group consisting of *B. anthracis* Sterne, *B. cereus* T strain, *B. thuringienesis* Kurstaki, *B. mycoides, B. subtilis* strain 168 (ATCC #23857) and *B. globigii*.

In some embodiments of this invention, in a step of identifying, the sample is determined to contain at least two *Bacillus* spore species and strains selected from the group consisting of *B. anthracis* Sterne, *B. cereus* T strain, *B. thuringienesis* Kurstaki, *B. mycoides, B. subtilis* strain 168 (ATCC #23857) and *B. globigii*.

In some embodiments of this invention, the bacterial spore sample is a non-purified preparation.

In some embodiments of this invention, the acid is at least one acid selected from the group consisting of organic acids and inorganic acids.

In some embodiments of this invention, the mass spectrometry is matrix-assisted laser desorption ionization time-of-flight mass spectrometry.

In some embodiments of this invention, the acid is an acid selected from the group consisting of acetic acid, trifluoroacetic acid, formic acid, nitric acid, hydrochloric acid, and hydrofluoric acid.

In some embodiments of this invention, an immobilized trypsin proteolytic enzyme is utilized.

In some embodiments, this invention is directed to a method of identifying a *Bacillus* species and strain in bacterial spores, comprising the steps of:
 preparing a bacterial spore sample on a matrix-assisted laser desorption ionization time-of-flight mass spectrometry sample holder;
 adding trifluoroacetic acid to said sample to extract small, acid-soluble proteins from the sample;
 digesting the small, acid-soluble proteins with trypsin to produce peptide fragments;
 subjecting the peptide fragments to matrix-assisted laser desorption ionization time-of-flight mass spectrometry including post source decay or collisional activation;
 subjecting the peptide fragments to matrix-assisted laser desorption ionization on a tandem mass spectrometer consisting of an ion trap interfaced to a time-of-flight analyzer;
 comparing results of the mass spectrometry of the peptide fragments with results or predicted results of mass spectrometry for known bacterial spore samples;
 identifying the bacterial spore sample as containing spores of at least one *Bacillus* species and strain by matching the results of the mass spectrometry of the peptide fragments with results or predicted results of mass spectrometry for peptide fragments from digested small, acid-soluble proteins from at least one bacterial spore sample having a known *Bacillus* species and strain.

In some embodiments, this invention is directed to a method of preparing a library of mass spectrometry data for single cell organisms or microorganisms, comprising the steps of:
 a) preparing a sample of at least one single cell organism or microorganism;
 b) adding a solvent to said sample to extract small, acid-soluble proteins from the sample;
 c) digesting the small, acid-soluble proteins with proteolytic enzyme to produce peptide fragments;
 d) subjecting the peptide fragments to mass spectrometry;
 e) repeating steps a) through d) for additional organisms or microorganisms;
 f) storing data results from the mass spectrometry for each organism or microorganism in an accessible location to form a library of said data results.

In some embodiments, this invention is directed to media comprising a database or protein or gene sequences of small, acid-soluble proteins determined for a plurality of different types of *Bacillus* spores.

BRIEF DESCRIPTION OF THE SEVERAL VIEWS OF THE DRAWINGS

Embodiments of this invention will now be described in detail with reference to the attached Figures, in which:

FIG. 1 shows a strategy for rapid identification of *Bacillus* spores and their mixtures by spore lysis on the sample holder, in situ proteolysis, $MS^n$ analysis and database searching;

FIG. 2 shows MALDI-TOFMS spectra from polypeptide ions (2*a*) and tryptic peptide ions (2*b*) generated in situ from *B. anthracis* Sterne spores;

FIG. 3 shows MALDI-TOFMS spectrum of peptide ions generated in situ from a 3:1 spore mixture of *B. thuringiensis* and *B. globigii;*

FIG. 4 shows PSD spectra from peptide ions at m/z 1929 (4*a*) and m/z 1940 (4*b*) derived from a 3:1 spore mixture of *B. thuringiensis* and *B. globigii;*

FIG. 5 shows MALDI-TOFMS spectrum of tryptic peptides generated in situ from a 1:1 spore mixture of *B. anthracis* sterne and *B. thuriengiensis;*

FIG. 6 shows post source decay mass spectrum of the tryptic peptide at m/z 1519;

FIG. 7 shows MALDI spectra of tryptic digests generated on probe from vegetative cells of *B. subtilis* 168 by enzymatic proteolysis for 5 and 20 min; and FIG. 8 shows fragmentation spectra of ions to demonstrate the high extent of sequence-specific information achievable by MALDI-PSD analysis.

DETAILED DESCRIPTION OF THE INVENTION

This invention combines selective solubilization of a limited set of proteins, such as SASPs, on a sample holder, with rapid enzymatic digestion in situ, tandem mass spectrometry and database searching to characterize organisms such as *Bacillus* spores, Gram positive vegetative bacteria, Gram negative vegetative bacteria, viruses, fungi, single celled parasites and other single celled organisms, that may or may not be contained in mixtures, and to distinguish such organisms including closely related species and strains.

Some embodiments of this invention provide identification of *Bacillus* spores based on the family of small acid soluble proteins abundant in each spore. Selective chemical solubilization is combined in situ with rapid specific cleavage, partial peptide sequencing by mass spectrometry and database searching. Specificity is enhanced by the construction of a limited database comprising small acid soluble proteins. An example approach is summarized in FIG. 1, which shows a strategy for rapid identification of *Bacillus* spores and their mixtures by spore lysis on the sample holder, selective solubilization, in situ proteolysis, $MS^n$ analysis and database searching.

The method is straightforward and does not require fractionation or protein isolation steps. Spore samples can be prepared directly, for example, on a MALDI sample slide in less than about 3 to 40 min as described below.

To the spore sample on the MALDI sample holder about 5 to 30%, for example 10% trifluoroacetic acid (TFA) in water is added. Other solvents including, for examples, methanol and aqueous ammonium acetate as well as inorganic and organic acids including acetic acid, formic acid, nitric acid, hydrochloric acid, hydrofluoric acid, and mixtures containing these solvents can and have been used successfully.

The solvent is selected to extract a limited, reproducible set of proteins from the sample. For example, a solvent can be selected that extracts a limited number of proteins, preferably 1-15 proteins, and more preferably 1-10 proteins, out of hundreds or thousands of proteins in the sample, while the remainder of the proteins are precipitated. The limited number of different proteins extracted can vary depending on the solvent and sample, but the number preferably ranges from 1-15, or any number or range within that range, such as 5-6. The set of proteins extracted is reproducible since each time a specific sample is treated with a specific solvent, the same number and set of proteins should be extracted.

The solution is allowed to dry before a proteolytic enzyme, such as trypsin immobilized on agarose beads, is added in buffer solution. Incubation (about 1 to 25 min) can be carried out in a closed or humidified chamber to control evaporation.

The product mixture can then be dried, and the digestion can be stopped, for example by adding, 0.5 μl of trifluoroacetic acid solution (1% in water), or by using any other method to denature the enzyme. In embodiments of this invention using MALDI, an appropriate MALDI matrix is added, for example a solution of α-cyano-4-hydroxycinnamic acid solution, 50 mM in 70% acetonitrile/0.1% trifluoroacetic acid to the digested spore sample to enable laser desorption of the peptide products. Of course any MALDI matrix could be used, such as ice.

Following the above method, successful production of tryptic peptide products has been confirmed by the present inventors with a MALDI time-of-flight mass spectrometer (Kratos MALDI 4) operating in linear mode; at 20 kV accelerating voltage and a delay time of 0.3 μs.

The feasibility of the method is demonstrated using a high performance time-of-flight mass spectrometer with a curved field reflectron (Shimadzu Biotech Axima-CRF), operated in the reflectron positive ion mode. Sequence specific information on peptides is provided by postsource decay analysis. Also with MALDI on a hybrid mass spectrometer including a quadrupole ion trap interfaced to a time-of-flight analyzer and using collisional activation to promote fragmentation of selected peptides.

Although the method of this invention is described with reference to MALDI, the method of this invention is compatible any type of mass spectrometry, such as with a MS/MS capable mass analyzer equipped with a MALDI ionization source. In addition to spontaneous (metastable) decomposition detected as post source decay, decomposition induced by collisions with a partial pressure of neutral gas, or various kinds of reactive collisions may also provide fragment or sequence ions for the database search.

In the MALDI process singly charged ions are formed primarily. Thus, MALDI mass spectra of even complex samples such as microorganisms are easily interpretable in terms of mass determination. Previous MALDI-MS studies focused on the analysis of characteristic biomarkers to identify bacterial spores. Since biomarker mass spectra are influenced by cell growth conditions and sample preparation methods, the identification process can be complicated (Demirev et al, Anal Chem 71, 2732, 1999).

In this invention, treatment of whole single cell organisms, such as and preferably bacterial spores, by acid selectively releases the small acid soluble spore protein family. Digestion of this limited set of proteins by a proteolytic enzyme, such as trypsin, and searching a protein/genome database provides a sensitive and reliable approach for identification of *Bacillus* spores. The use of a database limited to the small acid spore proteins further enhances the significance of matches.

Experiment 1.

An aliquot of 0.8 µl aqueous suspension of *B. anthracis* Sterne spores (non infectious veterinary strain) (2.5 mg/ml) was placed onto a MALDI sample holder and mixed with 1.2 µl diluted TFA (10% in water). The mixture was allowed to air dry before addition of 1 Pl of trypsin immobilized on agarose beads in 25 mM ammonium bicarbonate buffer solution. The sample was incubated for 25 min covered within a humidification chamber for digestion. By allowing the sample to dry and adding 0.5 µl of TFA solution (0.1% in water), digestion was stopped. An aliquot of 0.8 µl of α-cyano-4-hydroxycinnamic acid matrix solution (50 mM in 70 acetonitrile/0.1% TFA) was placed on the digested spore sample for MALDI mass spectrometric analysis.

Figure 1:
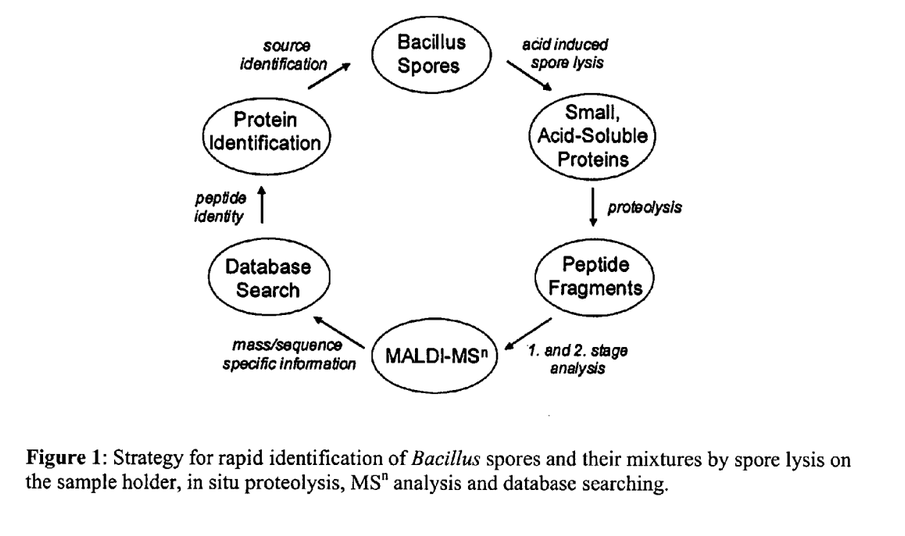
Figure 2:
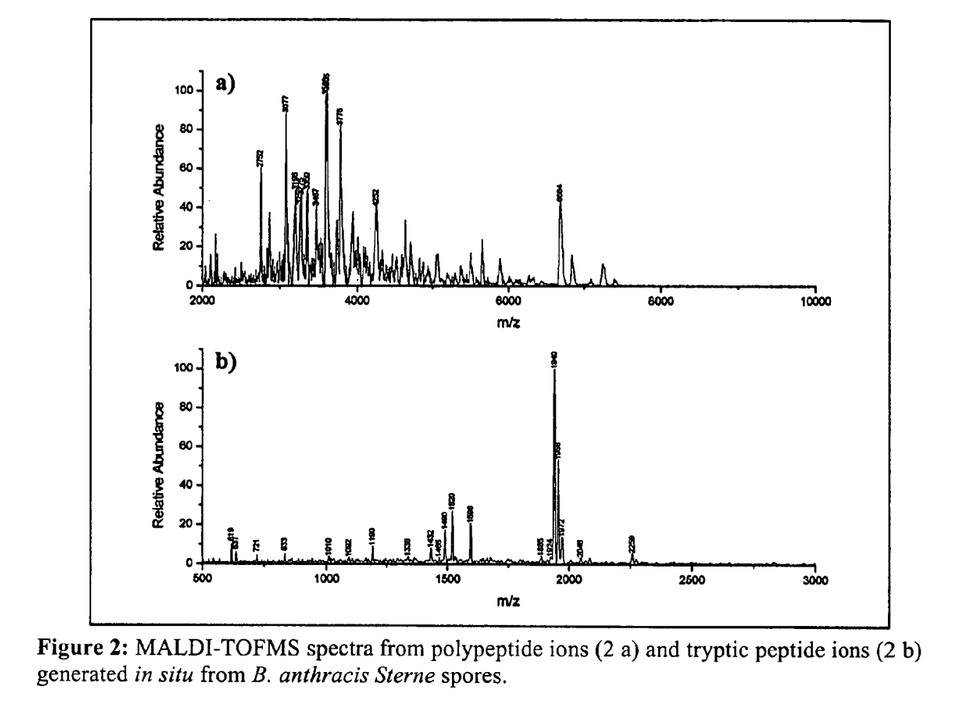

FIG. 2a shows the mass spectrum of *B. anthracis* Sterne spores as a result of on-slide spore lysis using 10% TFA. Ion signals at 6680 Da, 6835 Da, and 7083 Da have been previously identified as acid-soluble spore protein biomarkers from this spore species (Hahout, et al, Applied Environ. Microbiology, 69, in press, 2003). Digestion of acid treated *B. anthracis* Sterne spores as described before results in mass spectra showing intense peptide fragments of these specific biomarkers (FIG. 2b).

Ion signal intensities of tryptic peptides generated in situ are as much as 100 times more intense than corresponding protein biomarker signals by employing comparable experimental conditions. Since MALDI-TOFMS analysis of tryptic peptides can be readily performed in, the reflectron ion mode, mass resolution and accuracy is increased compared to protein profiling. A compilation of tryptic peptides generated in situ from a selection of *Bacillus* spore species is presented in table 1.

TABLE 1

Compilation of peptide fragment ions generated in situ from various *Bacillus* sores.

| *Bacillus* spore species and strain | Observed [M + H]+ ions* of tryptic peptides |
|---|---|
| *B. anthracis* Sterne | 1488, 1518, 1594, 1940, 1956, 1972, 2007, 2047, 2259 |
| *B. cereus* T strain | 1431, 1489, 1505, 1535, 1595, 1929, 1940, 1956, 1972, 2259, 2275 |
| *B. thuringiensis* Kurstaki | 1431, 1489, 1535, 1595, 1940, 1956, 1972 |
| *B. mycoides* | 1481, 1535, 1595, 1956, 1972 |
| *B. subtilis* strain 168, ATCC # 23857 | 802, 817, 920, 1322, 1338, 1419, 1640, 1881, 2286, 2442, 2784, 2842 |
| *B globigii* | 1817, 1929, 2557, 2687 2785 2828 |

*average masses

Experiment 2

Figure 3:
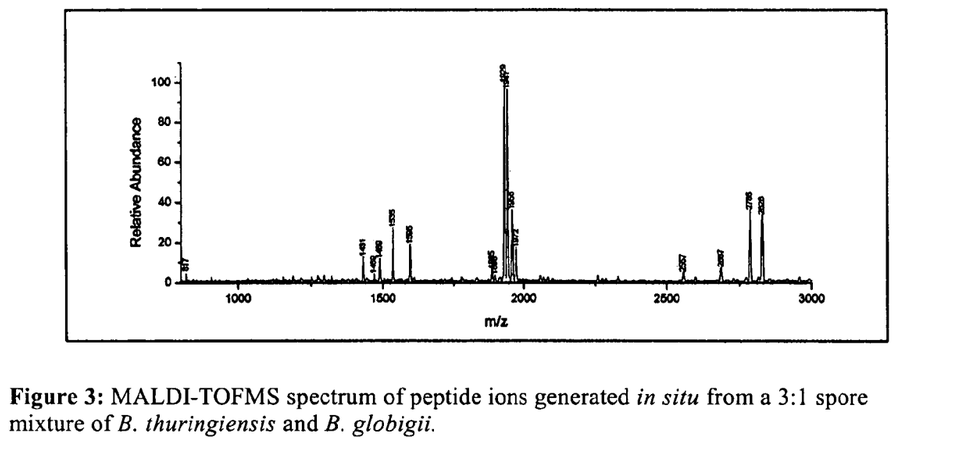

To enhance sample complexity, and therefore, relate to problems often encountered under field conditions, mixtures of two different *Bacillus* spore species were analyzed. As an example, the mass spectrum of tryptic peptides generated in situ from a 3:1 mixture of *B. thuringiensis* and *B. globigii* spores is shown in FIG. 3. No ion signal suppression of peptide fragments was observed in the MALDI-TOFMS spectrum with respect to peptide mass spectra generated from a single *Bacillus* spore species. This reflects the selective and predictable solubilization of only a limited set of proteins from each kind of spore. Characteristic peptide ions for *B. thuringiensis* spores are detected at m/z 1431, m/z 1489, m/z 1535, m/z 1595, m/z 1940, m/z 1956, and m/z 1972, whereas ions at m/z 817, m/z 1929, m/z 2557, m/z 2687, m/z 2785, m/z 2828 relate to *B. globigii* spores (see Table 1).

Figure 4:
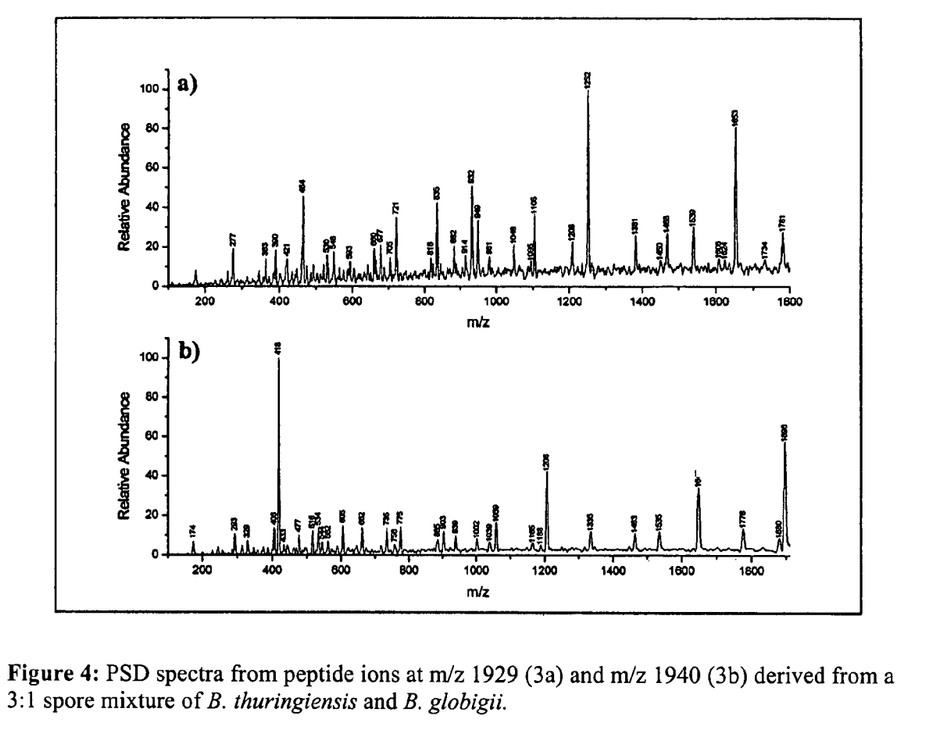

This invention moves beyond simple proteolytic peptide mass mapping, however, by providing sequence specific information on many individual peptides. In this experiment, sequence specific information was obtained from analyzing metastable decay processes of ions in a time-of-flight instrument. For these postsource decay (PSD) experiments, ions were isolated in a ±10 to 15 Da window with an ion gate. PSD spectra were acquired by irradiating the sample with 38 to 50% increased laser power. The capability of this technique is demonstrated on protonated tryptic peptide ions at m/z 1929 and m/z 1940 derived from the 3:1 spore mixture of *B. thuringiensis* Kurstaki and *B. globigii*, respectively (FIG. 4 and Table 1).

PSD spectra of both peptides (m/z 1929, m/z 1940) show extended fragmentation due to metastable decay. Peptide precursor and fragment ion mass values were exploited using the Mascot Sequence database query software available free on the internet. Typical search parameters used in this study are listed in Table 2.

TABLE 2

Database search parameters.

| Database | NCBInr |
|---|---|
| Taxonomy | Bacteria Eubacteria |
| Missed cleavages | <1 |
| Protein mass | Unrestricted |
| Fragment matches | b- and y-ion types |
| Peptide mass | +1 Da |
| Fragment ions | +1-1.5 Da |

Based on fragment ion information from the protonated peptide ions at m/z 1929, spore protein 1 (MW 7227) from *Geobacillus stearothermophilus* was identified with a score of 215, while other candidates had scores lower than 45. Generally, only protein scores greater than 69 are considered as significant hits. As a result of interrogation based on fragments of the protonated peptide at m/z 1940, two α/β-type spore proteins (MW 6805, 7290) were matched from *B. anthracis* A2012 and spore protein 2 (MW 6837) was matched from *B. cereus*, with scores between 194 and 195. Scores lower than 56 were shown for other candidates, reflecting insignificant matches. Since neither of the genomes of *B. globigii* and *B. thuringiensis* have been sequenced yet, these species could not be found in the database. Sequences for the small acid soluble proteins of these two species are also not present in the database at the present time. While less is known about *B. globigii*, *B. thuringiensis*, *B. anthracis*, and *B. cereus* represent closely related species (Helgason et al, Applied Environ Microbiol 66, 2627, 2000). Additional MS/MS studies of peptide fragments containing variant amino acids would be needed to clearly differentiate between these species. On the other hand, the example given demonstrates that *Bacillus* spore species can be differentiated in their mixtures based on a single in situ generated peptide of each species.

Experiment 3

The rapid identification of *B. anthracis* spores is a main focus of public interest. In this context, the differentiation between *B. anthracis* and *B. thuringiensis* spores, the latter a major contaminant in the troposphere, is crucial for a future implementation of the method described here in field studies. In this laboratory study, *B. anthracis* Sterne, a human non-pathogen (vaccine), serves as model organism for pathogenic *B. anthracis* strains. Genomes of the Sterne and Ames strains are assumed to be identical.

A 2:1 mixture of spores from *B. anthracis* Sterne and *B. thuringiensis* Kurstaki was prepared by placing 0.4 gl of each spore species on the MALDI sample plate. After on-slide spore lysis and direct digestion, peptide fragments were detected by MALDI-TOFMS analysis (FIG. 5).

Figure 5:
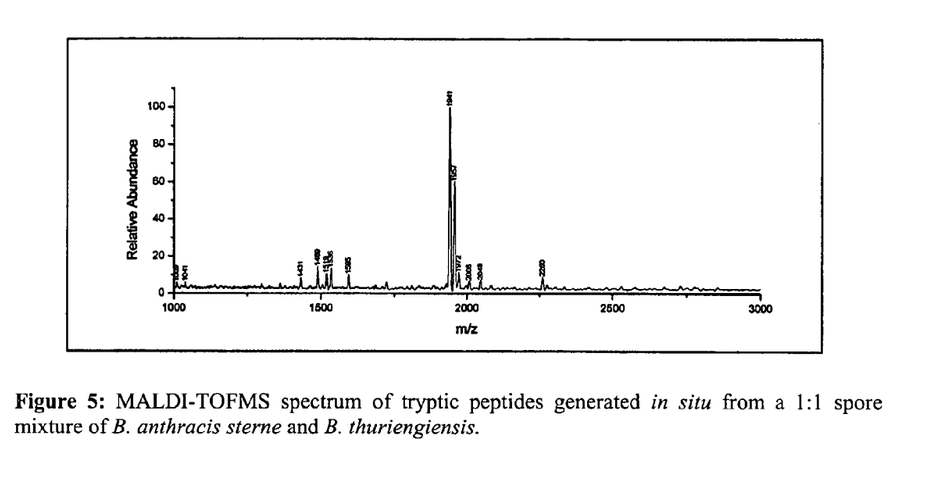
Figure 6:
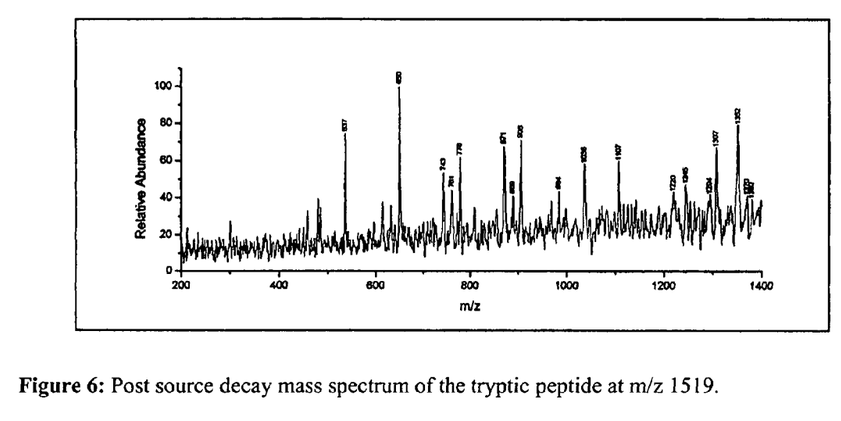

Although some peptide fragments with coincident mass-to-charge values are detected from the two spore species (see Table 1), the presence of *B. anthracis* Sterne spores is confirmed by PSD analysis of the protonated peptide at m/z 1519 (FIG. 5).

Based on the information provided by peptide fragmentation, the database was searched using Mascot sequence query. The α/β-type spore protein from *Bacillus anthracis* A2012 was matched with a score of 93, while other candidates had scores lower than 47.

A compilation of PSD fragment ions of selected peptides generated in situ from whole bacterial spores and results of the corresponding database searches is presented in Table 3. The results in Tables 1 and 3 indicate that differentiation of spores of *B. anthracis* Sterne, *B. subtilis*, *B. globigii*, *B. mycoides*, *B. cereus* T and *B. thuringiensis* Kurstaki is feasible.

TABLE 3

Compilation of PSD fragment ions of some tryptic peptides generated in situ from *Bacillus* sores and database search results. Protein scores greater than 69 are considered significant.

| [M + H]$^+$ | Fragment ions (average mass | Database search result |
|---|---|---|
| 1519 (BA) | 1307, 1245, 1220, 984, 906, 871, 778, 743, 650, 537, 485, 300 | gi|121402693, Mass: 6810, Total score: 93, Small, acid-soluble spore proteins, α/β-type SASP from *Bacillus anthracis* str. A2012. |
| 1881 (BS) | 1639, 1526, 1455, 1368, 1238, 1091, 1034, 935, 848, 821, 708, 580, 514, 464, 428, 421, 364, 356, 262, 243, 175 | gi|16078040, Mass: 6980, Total score: 191, Small acid-soluble spore protein, α/β-type SASP from *Bacillus subtilis*. gi|16080009, Mass: 7071, Total score: 191, Small acid-soluble spore protein, α/β-type SASP from *Bacillus subtilis*. |
| 1929 (BG) | 1781, 1653, 1539, 1468, 1381, 1252, 1208, 1105, 1048, 949, 932, 835, 721, 677, 593, 548, 464, 390, 363, 277, 262, 175 | gi|134224, Mass: 7227, Total score: 215, Small, acid-soluble spore protein, SASP 1 from *Geobacillus stearothermo-chilus*. |
| 1940 (BC, BT) | 1776, 1648, 1535, 1463, 1335, 1206, 1165, 1059, 1039, 1002, 939, 903, 775, 735, 662, 605, 534, 477, 418, 406, 293, 175 | gi|21402693, Mass: 6810, Total score: 195, Small, acid-soluble spore proteins, α/β-type from *Bacillus anthracis* str: A2012. gi|134231, Mass: 6842, Total score: 195, Small, acid-soluble spore proteins 2 from *Bacillus cereus*. gi|21401004, Mass: 7294, Total score: 194, Small, acid-soluble spore proteins, α/β-type from *Bacillus anthracis* str A2012. |
| 2785 (BG) | 2656, 2544, 2414, 2287, 2200, 2129, 2075, 1999, 1872, 1815, 1687, 1382, 1253, 1105, 1034, 947, 818, 717, 602 | gi|134246, Mass: 9020, Total score: 210, Small, acid-soluble spore proteins, γ-type from *Geobacillus stearothermophilus*. |
| 2842 (BS) | 2600, 2473, 2344, 2257, 2186, 2129, 1873, 1815, 1687, 1540, 1483, 1382, 1253, 1106, 1035, 819, 717, 602 | gi|16077932, Mass: 9268, Total score: 218, small acid-soluble spore protein, γ-type from *Bacillus subtilis*. |

With this approach, species-specific information is gained from various *Bacillus* spores and their mixtures. A predictable subset of proteins is selectively solubilized for the analysis. No isolation or fractionation of proteins from spore debris is needed. With both on-slide spore lysis and in situ digestion, equipment, time-consumption and sample amount are greatly reduced compared to using traditional protocols. The method is compatible with all MALDI-MS and MALDI MS/MS instruments, e.g., MALDI quadrupole TOF, MALDI-TOF/TOF, MALDI ion trap, MALDI ion trap-TOF, and MALDI-FTICR. It can be implemented with either post source decay or collision induced decomposition. Hence, the method can be widely employed.

Experiment 4

Vegetative cells of *B. subtilis* strain EMG 168, *B. cereus* strain T, *B. globigii* strain 9372, *B. thuringiensis* subs. Kurstaki strain HD-1 (ATCC 33679), *B. sphaericus* strain and *B. anthracis* Sterne, a non-pathogenic strain widely used as a vaccine for animals and lifestock, were suspended in a 1:1 mixture of MeOH and 25 mM ammonium bicarbonate buffer resulting in a final concentration of 2.5 mg of cells per milliliter. Aliquots of 0.8 µl of cell suspensions were directly placed on the MALDI plate, and bacterial samples were allowed to air dry (~2.5 min). Subsequently, 1 µl of immobilized trypsin in 25 mM ammonium bicarbonate buffer (pH≈7.5) was deposited on each sample for in situ proteolytic digestion of the protein subset solubilized from the cells.

The MALDI plate was covered with a humidification chamber (100% relative humidity) at room temperature to prevent sample drying. Cleavage reactions were stopped by adding 0.1% TFA for peptide analysis by matrix-assisted laser desorption/ionization time-of-flight (MALDI-TOF) mass spectrometry with α-cyano-4-hydroxycinnammic acid as MALDI matrix.

Using these conditions, extended enzymatic proteolysis of bacterial proteins were observed within 5 to 20 min providing tryptic peptides with ion signal intensities adequate for post-source decay (PSD) analysis with a curfed-field reflectron instrument (Kratos Analytical AXIMA-CFR supplied by Shimadzu Biotech, Manchester, U.K.).

MALDI MS and PSD spectra of high quality were acquired on the crude digests with no need of any further sample processing. Partial sequence information obtained from bacterial peptides by PSD was used for database searches in the NCBInr database taxonomically restricted to bacteria (eubacteria) via Mascot Sequence Query. Search parameters were usually set as follows: enzyme, trypsin; missed cleavages, 0; protein mass, unrestricted; product ion matches, b- and y-type ions; peptide ion mass tolerance, ±1.0 Da, product ion mass tolerance: ±1.5 Da.

Figure 7:
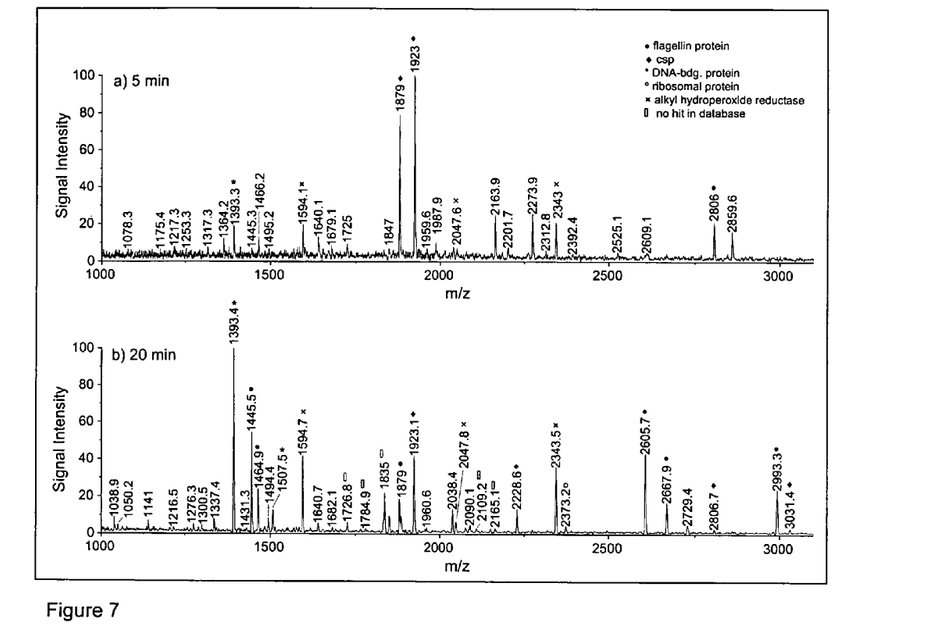

The wild-type species *Bacillus subtilis* 168 was studied as a genetically amenable, nonpathogenic model system to elaborate on the potential of microsequencing by PSD combined with database searches for the rapid identification of bacteria. The MALDI spectra of the tryptic digests generated on probe from vegetative cells of *B. subtilis* 168 by enzymatic proteolysis for 5 and 20 min are shown in FIG. 7. Peptide ions suitable for PSD analysis could be generated by tryptic digestion for 5 min. Formation of additional protonated peptides was observed by extending the digestion time to, e.g. 20 min, and well resolved peptide ion signals were found in the mass range of 1000 to 3100 Da. As digestion time was extended from 20 to 45 min, no significant change of the extend of proteolysis could be observed in the mass spectra.

To determine the identity of protein precursors, and, accordingly, their bacterial sources, distinct peptide ions were isolated with an ion gate set to a ±10 to 15-Da window, and PSD analysis of selected parent ions was performed by increasing the laser power by 40 to 50%. For most of the tryptic peptide ions from *B. subtilis* 168 extended metastable decay was observed in the field-free region, and PSD spectra could be obtained as a sum of about 150 laser shots.

Figure 8:
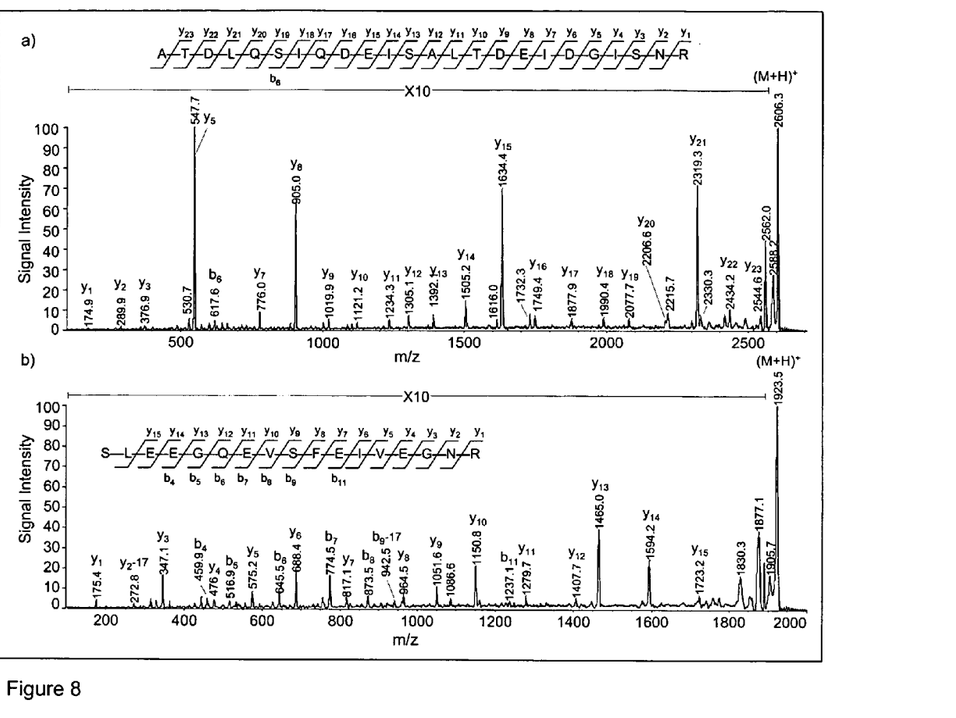

Fragmentation spectra of ions of 2606.3 Da and 1923.5 Da are shown to demonstrate the high extend of sequence-specific information achievable by MALDI-PSD analysis (FIG. 8 (a and b)), and product ions observed match b- and y-type ions. The latter referred to Y"-type ions according to the nomenclature introduced by Roepstorff and Fohlmann Since peptides with basic residues (Arg and Lys) on the C-terminal side are generated by protein cleavage with trypsin, formation of y-type ions is strongly favored, and cleavage of amino bonds containing glutamic acid and aspartic acid resulted in y-type ions with high abundances as reported before.

Uninterpreted PSD, and product ions were used with signal intensities at least 3% above the noise level were generically included in database searches with Mascot Sequence Query, making this identification process automatable.

Sequence information achieved from protonated peptides of 2606.3 Da and 1923.5 Da resulted in the identification of the flagellin and the cold-shock protein D (Csp-D) with Mascot scores up to 232, and *B. subtilis* 168 was retrieved from public databases as bacterial source for both proteins. The latter protein has been previously identified in a tryptic digest from a cellular extract of *B. subtilis* 168 via MALDI-PSD analysis. The identity of the flagellin protein could be further confirmed by partial sequencing of the protonated peptide of 2993.3 Da, and the detection of 4 additional tryptic peptides matching peptides from theoretical tryptic digests of the flagellin protein in mass as indicated in FIG. 7.

The capability of this approach to provide complete cleavage products of the 32.6 kDa flagellin protein in *B. subtilis* 168 by on probe tryptic digestion in 10 to 20 min is particularly appealing, since the genes encoding such proteins have been already successfully targeted as biomarkers in detection, population genetics, and epidemiological analysis. Since the flagellin protein exists in as many as 20.000 copies composing the filament of the bacterial flagellum, it represents a naturally amplified biomarker suitable to detect bacterial species at potentially low concentrations. The majority of eubacterial flagellin proteins comprise about 500 amino acids with highly conserved N- and C-terminal regions, and a central domain that can vary considerably in both amino acid sequence and size (Joys, 1988; Wilson&Beveridge, 1993).

The combination of considerable intra-species differences in amino acid sequence and the quantity of sequence data available makes flagellar variation a biomarker with widespread potential uses for the specific detection and identification of species or strains of motile bacteria.

Additional PSD analysis of protonated tryptic peptides of 1923.5, 1878.9, and 2806.9 Da resulted in the identification of major cold-shock protein (Csps) listed for *B. subtiltis* 168 in public databases. Since Csps in *B. subtilis* exhibit extended sequence homologies, only the CspD of 7303.1 Da could be specifically identified in the this work.

In general, Csps constitute a widespread and highly conserved protein family in bacteria, and multiple copies of Csps are often present (10, 25). *B. subtilis* contains three csp genes, and CspB, CspC and CspD comprise one of the highest accumulating protein group of *B. subtilis* after a temperature downshift (Graumann et al., 1996). It is proposed that these proteins play important roles in the adaptation of cells to low-temperature conditions (Graumann & Marahiel, 1999) by, e.g., keeping critical mRNAs accessible for the ribosomes at low-temperatures (Graumann et al., 1997; Schindler et al., 1999). Nonetheless, Csps in bacterial cells are also present at 37° C. (6, 9), and the presence of at least one Csp is necessary to maintain viability of *B. subtilis* at low and optimal growth temperatures, while depletion of Csps leads to compromised and deregulated protein synthesis (6).

To exclude accidentally induced overexpression of Csps in *B. subtilis* 168 by, for example, the storage of vegetative cells at −80° C. before use, a control experiment was performed, and cells not exposed to any temperature downshifts were prepared. For this purpose, cells were harvested, purified by repeated salt washes, and directly digested on probe with trypsin, yet, no significant change in mass and relative abundance of peptide ions could be observed in the MALDI spectra obtained (not shown) compared to the spectrum shown in FIG. 7*b*. Molecular masses of cold-shock proteins retrieved from searches in the NCBInr database range from 4977 Da to 7405 Da, and extended sequence homologies are exhibited within these proteins. In addition, the non-specific DNA-binding protein HBsu in *B. subtils* 168 as indicated in the MALDI spectrum shown in FIG. 7 was identified. Sequences of the non-specific DNA-binding proteins with molecular masses of 9897.38 Da in *B. subtilis* 168 and of 9884.29 Da in *B. globigii* differ only in a single amino acid, and in silico digests with trypsin reveal only one unique peptide for these proteins each with a mass below 450 Da.

What is claimed is:

1. A method of analyzing or identifying single cell organisms or microorganisms, comprising the steps of:
    preparing a sample of at least one single cell organism or microorganism on a matrix assisted laser desorption ionization (MALDI) sample holder;
    adding an acid solvent to said sample on the MALDI sample holder to extract selectively a reproducible set of acid soluble proteins from the sample, said acid selected from the group consisting of trifluoroacetic acid, acetic acid, and formic acid;
    drying the sample extracted acid soluble proteins on the MALDI sample holder;
    digesting the reproducible set of acid soluble proteins in situ on said MALDI sample holder with a buffered proteolytic enzyme or with a chemical reagent that cleaves said proteins at specific residues, to produce peptide fragments in situ on the sample holder, where said digesting step is carried out for a time period of from 1 to 25 minutes;
    subjecting the peptide fragments on the MALDI sample holder to mass spectrometry and tandem mass spectrometric analysis to obtain mass spectra corresponding to said peptide fragments;
    determining at least partial sequences of at least some of the peptide fragments from said mass spectra; and
    identifying said acid soluble proteins and thus the single cell organism or microorganism by comparison to information in databases either constructed by analysis of pure microorganisms or constructed in silico from gene and protein sequences.

2. The method of claim 1 wherein said single cell organism or microorganism is at least one member selected from the group consisting of bacterial spores, gram positive vegetative bacteria, gram negative vegetative bacteria, virus, fungus, single cell parasites, and any mixtures thereof.

3. The method of claim 1 wherein said proteolytic enzyme is selected from the group consisting of trypsin, chymotrypsin, pepsin, subtilisin, papain, elastase, *S. aureus* V8, Lys-C endoproteinase, Arg-C endoproteinase, and Glu-C endoproteinase; or wherein said chemical reagent is selected from the group consisting of BNPS-skatole and cyanogen bromide.

4. The method of claim 1 wherein both the mass spectrometry and tandem mass spectrometric analysis are conducted using matrix-assisted laser desorption ionization time-of-flight mass spectrometer.

5. A method of identifying microorganisms or bacterial spores, comprising the steps of:
preparing a microorganism or bacterial spore sample to be identified on a MALDI sample holder;
adding an acid solvent to said sample on the MALDI sample holder to extract selectively a limited set of acid soluble proteins from the sample;
drying the sample extracted acid soluble proteins on the MALDI sample holder;
digesting the limited set of acid soluble proteins in situ on said MALDI sample holder with buffered proteolytic enzymes to produce peptide fragments in situ on the sample holder, where said digesting step is carried out for a time period of from 1 to 25 minutes;
subjecting the peptide fragments on the MALDI sample holder to mass spectrometry analysis to obtain mass spectra corresponding to said peptide fragments;
determining at least partial sequences for at least some of the peptide fragments from said mass spectra;
comparing the results of the mass spectrometry analysis of the peptide fragments with results of mass spectrometry for known bacterial spore samples; and
identifying the microorganism or bacterial spore sample by matching the results of the mass spectrometry analysis of the peptide fragments with results of mass spectrometry for peptide fragments from digested small, acid soluble proteins from at least one microorganism or bacterial spore sample having a known identity, or with sequences in databases of protein and gene sequences using at least one search algorithm.

6. The method of claim 5, wherein said microorganism or bacterial spore sample to be identified is from at least one member of the *Bacillus* genus and wherein said limited set of proteins are small, acid-soluble proteins.

7. The method of claim 6, wherein in said step of identifying, the results of the mass spectrometry of the peptide fragments of the sample spores are compared with the results of mass spectrometry of peptide fragments of spores of small, acid-soluble proteins from at least one *Bacillus* spore species and strain selected from the group consisting of *B. anthracis* Sterne, *B. cereus* T strain, *B. thuringienesis* Kurstaki, *B. mycoides, B. subtilis* strain 168 (ATCC #23857) and *B. globigii*.

8. The method of claim 7, wherein in said step of identifying, the sample to be identified is determined to contain one *Bacillus* spore species and strain selected from the group consisting of *B. anthracis* Sterne, *B. cereus* T strain, *B. thuringienesis* Kurstaki, *B. mycoides, B. subtilis* strain 168 (ATCC #23857) and *B. globigii*.

9. The method of claim 7, wherein in said step of identifying, the sample to be identified is determined to contain at least one *Bacillus* spore species and strains selected from the group consisting of *B. anthracis* Sterne, *B. cereus* T strain, *B. thuringienesis* Kurstaki, *B. mycoides, B. subtilis* strain 168 (ATCC #23857) and *B. globigii*.

10. The method of claim 7, wherein in said step of identifying, the sample to be identified is determined to contain at least two *Bacillus* spore species and strains selected from the group consisting of *B. anthracis* Sterne, *B. cereus* T strain, *B. thuringienesis* Kurstaki, *B. mycoides, B. subtilis* strain 168 (ATCC #23857) and *B. globigii*.

11. The method of claim 5, wherein said microorganism or bacterial spore sample to be identified is a non-purified preparation.

12. The method of claim 5, wherein said solvent is at least one member selected from the group consisting of an aqueous solution of an organic acid or an inorganic acid, acetic acid, trifluoroacetic acid, formic acid, nitric acid, hydrochloric acid, hydrofluoric acid, and any mixtures thereof.

13. The method of claim 5, wherein said mass spectrometry is matrix-assisted IR or UV laser desorption ionization time-of-flight mass spectrometry, and water or any other matrix is used.

14. The method of claim 5, wherein said proteolytic enzyme is selected from the group consisting of trypsin, chymotrypsin, pepsin, subtilisin, papain, elastase, *S. aureus* V8, Lys-C endoproteinase, Arg-C endoproteinase, and Glu-C endoproteinase.

15. A method of identifying a *Bacillus* species and strain in bacterial spores comprising the steps of:
preparing a bacterial spore sample on a matrix-assisted laser desorption ionization time-of-flight MALDI sample holder;
adding trifluoroacetic acid to said sample on the MALDI sample holder to extract small, acid-soluble proteins from the sample;
digesting the small acid-soluble proteins in situ on said MALDI sample holder with buffered trypsin to produce peptide fragments in situ on the MALDI sample holder, where said digesting step is carried out for a time period of from 1 to 25 minutes;
subjecting the peptide fragments on the MALDI sample holder to matrix-assisted laser desorption ionization time-of-flight mass spectrometry wherein any matrix is used;
comparing results of the mass spectrometry of the peptide fragments with results of mass spectrometry for known bacterial spore samples or with sequences in global or customized databases of protein or gene sequences;
identifying the bacterial spore sample as containing spores of at least one *Bacillus* species and strain by matching the results of the mass spectrometry of the peptide fragments with sequences for peptide fragments from digested small, acid-soluble proteins from at least one bacterial spore sample having a known *Bacillus* species and strain.

* * * * *